US010145842B2

(12) United States Patent
Coffey et al.

(10) Patent No.: US 10,145,842 B2
(45) Date of Patent: Dec. 4, 2018

(54) MICROFLUIDIC DEVICE, SYSTEM AND METHOD

(71) Applicant: Quidel Cardiovascular Inc., San Diego, CA (US)

(72) Inventors: William Patrick Coffey, Encinitas, CA (US); Paul Michael Crivelli, San Diego, CA (US); Austin Matthew Derfus, Carlsbad, CA (US); Tuan Hoang Do, San Diego, CA (US); Remus Anders Brix Haupt, Encinitas, CA (US); Emily Parker, Encinitas, CA (US); Gregory Reneff, San Diego, CA (US); Armando Raul Tovar, San Diego, CA (US)

(73) Assignee: Quidel Cardiovascular Inc., San Diego, CA (US)

( * ) Notice: Subject to any disclaimer, the term of this patent is extended or adjusted under 35 U.S.C. 154(b) by 741 days.

(21) Appl. No.: 14/391,643

(22) PCT Filed: Apr. 5, 2013

(86) PCT No.: PCT/US2013/035505
§ 371 (c)(1),
(2) Date: Oct. 9, 2014

(87) PCT Pub. No.: WO2013/154946
PCT Pub. Date: Oct. 17, 2013

(65) Prior Publication Data
US 2015/0087079 A1     Mar. 26, 2015

Related U.S. Application Data

(60) Provisional application No. 61/622,987, filed on Apr. 11, 2012.

(51) Int. Cl.
*G01N 31/00* (2006.01)
*G01N 33/53* (2006.01)
*G01N 33/543* (2006.01)

(52) U.S. Cl.
CPC . *G01N 33/54306* (2013.01); *G01N 33/54366* (2013.01); *B01L 2200/0621* (2013.01); *B01L 2300/0681* (2013.01); *B01L 2300/0816* (2013.01); *B01L 2300/0874* (2013.01); *B01L 2300/0883* (2013.01); *B01L 2400/0406* (2013.01); *B01L 2400/0487* (2013.01); *B01L 2400/0688* (2013.01)

(58) Field of Classification Search
None
See application file for complete search history.

(56) References Cited

U.S. PATENT DOCUMENTS

| 6,117,396 | A  | * | 9/2000  | Demers    | B01J 19/0046 |
|           |    |   |         |           | 222/394       |
| 7,213,473 | B2 | * | 5/2007  | Mosier    | B01L 3/0293  |
|           |    |   |         |           | 73/861.52    |
| 7,824,611 | B2 | * | 11/2010 | Buechler  | B01L 3/50273 |
|           |    |   |         |           | 422/425      |
| 8,747,779 | B2 | * | 6/2014  | Sprague   | B01L 3/502   |
|           |    |   |         |           | 422/407      |
| 9,011,797 | B2 | * | 4/2015  | Gilbert   | B01L 3/502738|
|           |    |   |         |           | 251/61.1     |
| 2002/0086436 | A1 |  | 7/2002  | Buechler  |              |
| 2004/0219072 | A1 |  | 11/2004 | Yamakawa et al. |       |
| 2007/0042427 | A1 |  | 2/2007  | Gerdes et al. |          |
| 2009/0053732 | A1 |  | 2/2009  | Vermesh et al. |         |
| 2010/0261286 | A1 |  | 10/2010 | Kim et al. |             |
| 2011/0045492 | A1 |  | 2/2011  | Bau-Madsen et al. |      |

FOREIGN PATENT DOCUMENTS

WO    2006042332 A2    4/2006

OTHER PUBLICATIONS

Stone et al. (Annu. Rev. Fluid Mech. 2004, vol. 36, pp. 381-411).*
Xue et al. (Applied mathematical Modelling, vol. 36 (2012) pp. 743-755).*
International Search Report, dated Jul. 19, 2013 (dated Jul. 19, 2013), the entire document.

* cited by examiner

*Primary Examiner* — Lisa V Cook
(74) *Attorney, Agent, or Firm* — McDermott Will & Emery LLP

(57) ABSTRACT

A combination of capillary forces and gas pressure is used to control the movement of liquid samples within a microfluidic device. A liquid sample introduced to a proximal portion of a capillary channel of a microfluidic device moves by capillary action partway along the capillary channel. As the liquid sample moves, a pressure of a gas acting upon a distal gas-liquid interface of the liquid sample increases by an amount sufficient to stop further movement of the liquid sample. To initiate further movement of the liquid sample, a pump connected to a distal portion of the capillary channel decreases the pressure of the gas acting upon the distal gas-liquid interface of the liquid sample by an amount sufficient to permit the liquid sample to move by capillary action further along the capillary channel of the microfluidic device.

30 Claims, 12 Drawing Sheets

MICROFLUIDIC DEVICE, SYSTEM AND METHOD

CLAIM FOR PRIORITY

This application claims priority under 35 USC 371 to International Application No, PCT/US2013/035505, filed Apr. 5, 2013, which claims priority to U.S. Provisional Patent Application No. 61/622,987, filed Apr. 11, 2012, each of which is hereby incorporated by reference in its entirety.

BACKGROUND OF THE INVENTION

Field of the Invention

The present invention relates to microfluidics, and more particularly to a microfluidic device, system and method for control of fluid flow.

Background Information

Microfluidics relates to the manipulation of small volumes of one or more fluids, e.g., gases and/or liquids. The total volume of fluid may be, e.g., about 250 microliters or less, e.g., about 125 microliters or less, about 75 microliters or less, about 50 microliters or less, or about 25 microliters or less.

The use of microfluidics to determine the presence of at least one target in a liquid sample is known. For example, U.S. Pat. No. 7,824,611, which is incorporated herein by reference in its entirety, discloses immunological assay devices, assay systems and device components having at least two opposing surfaces disposed a capillary distance apart, at least one of which is capable of immobilizing at least one target ligand or a conjugate in an amount related to the presence or amount of target ligand in the sample from a fluid sample in a zone for controlled fluid movement to, through or away the zone. The 7,824,611 patent further discloses the use of reagents, such as receptors and conjugates, and biosensors, such as electrochemical, optical, electro-optical, or acoustic mechanical devices, to determine the presence of one or more targets.

SUMMARY OF THE INVENTION

In one embodiment, the present invention relates to a method for manipulating a liquid sample within a microfluidic device. The method includes moving the liquid sample by capillary action along a capillary channel of the microfluidic device and then increasing a pressure of a gas acting upon a distal gas-liquid interface of the liquid sample by an amount sufficient to stop the movement of the liquid sample along the capillary channel. The pressure of the gas acting upon the distal gas-liquid interface of the liquid sample is decreased by an amount sufficient to permit the liquid sample to move by capillary action further along the capillary channel of the microfluidic device. The steps of moving the liquid sample by capillary action, increasing the pressure, and then decreasing the pressure may be repeated one or more times. In embodiments, the liquid sample contacts a dried reagent disposed within the capillary channel during the step of moving the liquid sample. In a subsequent step of moving the sample, the liquid sample may contact a detection zone disposed within the microfluidic device. The method may further include determining the presence of one or more targets in a liquid sample.

The method may employ, for example, immunology (such as through the use of antibodies) and/or electrochemistry to determine the presence of the one or more targets. The method includes: introducing the liquid sample to a proximal portion of a capillary flow channel; advancing the liquid sample at a first flow rate toward a distal portion of the capillary flow channel until at least a distal gas-liquid interface of the liquid sample contacts a conjugate disposed in dry form within the capillary flow channel, the conjugate comprising a binding agent having an affinity for the target; subsequently, by increasing a gas pressure differential between a proximal gas-liquid interface of the liquid sample and the distal gas-liquid interface of the liquid sample, advancing the liquid sample at a second flow rate toward the distal portion of the capillary flow channel until at least the distal gas-liquid interface contacts a detection zone within the capillary flow channel, the detection zone comprising a second binding agent having an affinity for a complex comprising the conjugate and the target, the second flow rate being slower than the first flow rate; and subsequently, by increasing the gas pressure differential between the proximal and distal gas-liquid interfaces of the liquid sample, advancing the liquid sample a third flow rate toward the distal portion of the capillary flow channel until at least a majority of conjugate is (a) bound to the second binding agent and/or been advanced beyond the detection zone toward the distal end of the capillary flow channel.

In any of the foregoing embodiments, the capillary flow channel may be disposed within a microfluidic device.

The method of any of the foregoing embodiments may, further comprise, after the step of introducing the liquid sample, advancing the liquid sample by capillary flow along the capillary flow channel until the gas pressure acting upon the distal gas-liquid interface stops the liquid sample from advancing further along the capillary flow channel.

In any of the methods of any of the foregoing embodiments the liquid sample may be stopped prior to contacting the conjugate.

In any of the methods of any of the foregoing embodiments the liquid sample may be stopped after contacting the conjugate.

In any of the methods of any of the foregoing embodiments the method may further comprise providing a fluidic connection between a pump and a distal portion of the capillary flow channel. The step of providing a fluidic connection may be performed prior to the step of introducing the liquid sample. In any of the methods of any of the foregoing embodiments, the method may comprise terminating the fluidic connection between the pump and the distal portion of the capillary flow channel and then detecting conjugate present in the detection zone. The step of detecting the conjugate may comprise placing the microfluidic device in operable association with an optical reader for the microfluidic device. The step of detecting the conjugate may comprise using a biosensor to detect the conjugate. The biosensor may be an electrochemical, optical, electro-optical, or acoustic mechanical detector.

The step of providing the fluidic connection may comprise automatically positioning a proximal opening of the pump with respect to a distal opening of the capillary flow channel.

In any of the methods of any of the foregoing embodiments the steps of "increasing a gas pressure differential" may be performed by increasing a volume of gas in communication with the distal gas-liquid interface of the liquid sample.

In any of the methods of any of the foregoing embodiments the steps of "increasing a gas pressure differential" may be performed by actuating the pump. In any of the methods of any of the foregoing embodiments actuating the pump may increase a volume of gas in communication with the distal gas-liquid interface of the liquid sample. The pump may be a syringe pump.

In any of the methods of any of the foregoing embodiments, the liquid sample may experience a capillary force within the capillary flow channel and the magnitude of a force applied to the liquid sample by the "gas pressure differential" may be less than about 15 times the magnitude of the capillary force, e.g., less than about 10 times the magnitude of the capillary force, e.g., less than about 5 times the magnitude of the capillary force.

In any of the methods of any of the foregoing embodiments the method may further include the step of detecting conjugate bound to the detection zone. The step of detecting may be performed while a volume of the detection zone is filled with liquid sample. In any of the methods of any of the foregoing embodiments the detection zone may have a volume and the step of detecting may be performed after removing a majority of the liquid sample from the detection zone. The step of detecting may be performed while a majority of the volume of the detection zone is occupied by a gas. The step of detecting may be performed without first introducing a liquid other than the liquid sample into the detection zone. The step of detecting the conjugate may comprise using a biosensor to detect the conjugate. The biosensor may be an electrochemical, optical, electro-optical, or acoustic mechanical detector.

In any of the methods of any of the foregoing embodiments the liquid sample may comprise a biological sample obtained from a mammal. For example, biological sample may comprise blood or urine. The liquid sample may comprise a reagent. The liquid sample may be formed by combining the reagent and the biological sample. The step of combining may be performed prior to introducing the biological sample to the capillary flow channel.

In any of the methods of any of the foregoing embodiments the liquid sample may be a filtered liquid sample formed by passing a liquid sample through a filter. The filter may be any of the filters described herein. The filter may comprise pores and a size of the pores may decrease proceeding from a proximal face of the filter toward a distal face of the filter. In any of the methods of any of the foregoing embodiments the filtered liquid sample may comprise plasma and the step of passing the liquid sample through the filter may comprise filtering red blood cells from the liquid sample. In any of the methods of any of the foregoing embodiments the biological sample may be blood obtained from a finger of a human being. In any of the methods of any of the foregoing embodiments the liquid sample may be prepared from a total volume of blood of about 75 microliters or less, 50 microliters or less, 30 microliters or less, 20 microliters or less, such as about 15 microliters or less, such as about 10 microliters or less.

In any of the methods of any of the foregoing embodiments the total volume of the liquid sample may be about 75 microliters or less, 50 microliters or less, 30 microliters or less, 20 microliters or less, such as about 15 microliters or less, such as about 10 microliters or less.

In any of the methods of any of the foregoing embodiments, prior to the step of introducing the liquid sample, a distal opening of the capillary flow channel may be open to the atmosphere, and the method may further comprise closing the distal opening of the capillary flow channel off from the atmosphere. The step of closing off may be performed prior to introducing the liquid sample. The step of closing off may be automatically after or concurrently with a step of positioning the capillary flow channel in operable relation with a reader configured to operate the capillary flow channel to determine the presence of the at least one target in the liquid sample. The step of closing off may be performed by fluidically connecting the distal opening of the capillary flow channel and a pump, e.g., by forming a gas tight seal between the distal opening of the capillary flow channel and a pump. The pump may be a syringe pump.

In another embodiment, the present invention relates to a microfluidic system, comprising a capillary flow channel comprising a proximal opening and a distal opening; a dry reagent and a detection zone disposed within the capillary flow channel, the detection zone being disposed distal to the dry reagent; a pump in fluidic communication with the distal opening of the capillary flow channel; a liquid sample disposed within a proximal portion of the capillary flow channel, the liquid sample comprising a gas-liquid interface disposed within the capillary flow channel proximal to the reagent; and a gas disposed within the capillary flow channel distal to the gas-liquid interface of the liquid sample, the gas exerting a pressure on the gas-liquid interface of the liquid sample, the pressure being sufficient to prevent the liquid sample from advancing along the capillary flow channel toward the reagent.

In any microfluidic system of any of the foregoing embodiments, the microfluidic system may further comprise a controller configured to operate the pump to decrease the gas pressure in the capillary flow channel by an amount sufficient to cause the liquid sample to advance along the capillary flow channel until at least the gas-liquid interface of the liquid sample contacts the reagent. The controller may be configured to operate the pump to decrease the gas pressure in the capillary flow channel by an amount sufficient to cause the liquid sample to advance along the capillary flow channel until all of the reagent has been contacted by at least some of the liquid sample. In any microfluidic system of any of the foregoing embodiments the liquid sample may experience a capillary force within the capillary flow channel. In any microfluidic system of any of the foregoing embodiments the magnitude of the pressure may be sufficient to prevent the liquid sample from advancing along the capillary flow channel toward the reagent is substantially equal to the magnitude of the capillary force experienced by the liquid sample. The controller may be configured to operate the pump to increase a volume of gas in fluidic communication with the gas disposed within the capillary flow channel by an amount sufficient to allow the liquid sample to advance a desired distance along the capillary flow channel.

In any microfluidic system of any of the foregoing embodiments the system may comprise a reader configured to receive the capillary flow channel and determine the presence of one or more targets in the liquid sample. The reader may be configured to automatically position the pump in fluidic communication with the distal opening of the capillary flow channel. The reader may be configured to automatically move the pump away from the distal opening of the capillary flow channel prior to determining the presence of the one or more targets in the liquid sample. The reader may be configured to position an optical excitation source and an optical detector in optical communication with the detection zone after moving the pump away from the distal opening of the capillary flow channel. The reader may employ a biosensor to detect the target. The biosensor may be an electrochemical, optical, electro-optical, or acoustic mechanical detector.

In any microfluidic system of any of the foregoing embodiments the reagent may comprise a conjugate comprising a detectable label and a binder for a target. The detection zone may comprise a binder for the target or a complex of the conjugate and the target.

In any microfluidic system of any of the foregoing embodiments the system may comprise a microfluidic device and the capillary flow channel may be disposed within the microfluidic device.

In any microfluidic system of any of the foregoing embodiments the capillary flow channel may be configured to receive a total volume of liquid sample of less than about 75 microliters or less, 50 microliters or less, 30 microliters or less, 20 microliters or less, such as about 15 microliters or less, such as about 10 microliters or less.

In any microfluidic system of any of the foregoing embodiments the system may further comprise a filter in fluidic communication with a proximal portion of the capillary flow channel, the filter being configured to filter red blood cells from a sample comprising blood and the liquid sample comprises blood from which the red blood cells have been removed. The filter may be any of the filters disclosed herein.

Another embodiment of the present invention relates to a method for determining the presence of at least one target in a liquid sample. The method may comprise receiving a sample of blood obtained from a patient; introducing the at least a portion of the blood sample to a filter of a microfluidic device, a distal portion of the filter being in fluidic contact with a proximal portion of a capillary flow channel disposed within the microfluidic device, the filter configured to separate red blood cells from a liquid portion of the blood sample; allowing at least a portion of the liquid portion of the blood sample to advance toward a distal portion of the capillary flow channel until a gas pressure acting upon a distal gas-liquid interface of the liquid portion of sample stops the liquid portion from advancing further; subsequently, decreasing the gas pressure acting upon the distal gas-liquid interface to permit the liquid portion of sample to advance a further distance along the capillary flow channel; and subsequently, determining the presence of the target in the liquid portion of sample within the capillary flow channel. The filter may be any of the filters disclosed herein.

The method for determining the presence of a target in a liquid sample may comprise positioning a microfluidic device in an operable relation with a reader for the microfluidic device, the microfluidic device comprising a capillary flow channel comprising a proximal opening and a distal opening; positioning a pump in fluidic relation to the distal portion of the capillary flow channel; introducing a liquid sample to the proximal portion of the capillary flow channel, the liquid sample advancing by capillary flow along only a portion of the capillary flow channel until a gas pressure acting upon a distal gas-liquid interface of the liquid sample prevents the liquid sample from advancing further along the capillary flow channel; actuating a pump to decrease the pressure of gas acting upon the distal gas-liquid interface of the liquid sample so that the liquid sample advances a further distance along the capillary flow channel; and determining the presence of the target in the liquid sample within the capillary flow channel.

In any of the foregoing methods for determining the presence of a target in a liquid sample the method may further comprise disconnecting the pump from fluidic relation to the distal portion of the capillary flow channel prior to determining the presence of the target in the liquid sample.

In any of the foregoing methods for determining the presence of a target in a liquid sample the step of actuating the pump may comprise first actuating the pump a first rate to cause the liquid sample to advance at a first rate along the capillary flow channel and then actuating the pump at a second higher rate to cause the liquid sample to advance at a second higher rate along the capillary flow channel.

In any of the foregoing methods for determining the presence of a target in a liquid sample the step of determining may be employed using a biosensor. The biosensor may be an electrochemical, optical, electro-optical, or acoustic mechanical detector.

In another embodiment, the present invention relates to a filter, the filter having an upper surface, a lower surface and a perimeter; and a substrate having a surface, the lower surface of the filter and the surface of the substrate defining a spatially-dependent capillarity therebetween, the capillarity decreasing from a central portion of the lower surface of the filter toward the perimeter along at least two opposed directions.

At least a portion of the surface of the substrate may be convex and/or tapered.

In any of the foregoing filters, a gap between the lower surface of the filter and the surface of the substrate may increase from a central portion of the lower surface of the filter toward the perimeter along at least two opposed directions. In each of the opposed directions, the gap may increase from about 10 microns, e.g., about 15 microns, about 20 microns. In each of the opposed directions, the gap may increase to about 50 microns, to about 75 microns, to 100 microns, to about 200 microns, to about 300 microns, to about 500 microns. In each of the opposed directions, the gap may increase over a lateral distance of at least about 750 microns, at least about 1500 microns, at least about 2000 microns. In each of the opposed directions, the gap may increase over a distance of about 5000 microns or less, about 3000 microns or less, about 2500 microns or less.

In any of the foregoing filters, a portion of the surface of the substrate may contact a central portion of the lower surface of the filter.

In any of the foregoing filters, the filter may have a length and a width, and the portion of the surface of the substrate may contact the central portion of the lower surface of the filter along substantially all of the length of the filter. The length of the filter may be at least about 1.25 times, e.g., at least about 1.5 times, at least about 2.0 times as great as the width of the filter. The length of the filter may be about the same as the width of the filter. The length of the filter may be at least about 2 mm, e.g., at least about 3 mm, e.g., at least about 5 mm, e.g., at least about 7.5 mm, e.g., at least about 10 mm. The length of the filter may be about 15 mm or less, e.g., about 10 mm or less. The width of the filter may be at least about 2 mm, e.g., at least about 2 mm, e.g., at least about 3 mm, e.g., at least about 5 mm, e.g., at least about 7.5 mm, e.g., at least about 10 mm. The width of the filter may be about 15 mm or less, e.g., about 10 mm or less, about 7.5 mm or less, about 5 mm or less.

In any of the foregoing filters in which a portion of the surface of the substrate contacts the lower surface of the filter, the surface of the substrate may contact the lower surface of the filter along less than about half of the width of the filter, e.g., less than about one quarter the width of the filter, e.g., less than about ⅛ of the width of the filter. In any of the foregoing filters in which a portion of the surface of the substrate contacts the lower surface of the filter, the surface of the substrate may contact the lower surface of the filter along at least about half of the length of the filter, e.g., at least about ¾ of the length of the filter, e.g., at least about ⅘ of the length of the filter, at least about 9/10 of the length of the filter, e.g., substantially all of a length of the filter. The portion of the substrate that contacts the lower surface of the filter may contact the filter along a length of the filter of at least about 1 mm, at least about 2 mm, at least about 5 mm, at least about 7.5 mm, at least about 10 mm. The portion of the substrate that contacts the lower surface of the filter may contact the filter along a width of the filter of at least about 100 microns, at least about 200 microns, at least about 300 microns, at least about 500 microns. The portion of the substrate that contacts the lower surface of the filter may contact the filter along a width of the filter of about 1000 microns or less, about 750 microns or less, about 500 microns or less.

In any of the foregoing filters, a portion of the surface of the substrate may contact the central portion of the lower surface of the filter along a first dimension of the filter and along a second dimension of the filter and wherein the distance contacted along the first dimension of the filter may be at least about 5 times greater, at least about 7.5 times greater, at least about 10 times greater, than along the second dimension of the filter, and wherein the first and second dimensions may be perpendicular.

Any of the foregoing filters may further comprise a capillary flow channel having an opening in fluidic communication with a space between the lower surface of the filter and the surface of the substrate.

Any of the foregoing filters may further comprise a vent in fluidic communication with a space between the lower surface of the filter and the surface of the substrate. The opening of the capillary channel and the vent may be spaced apart by substantially all of a length or width of the filter.

Any of the foregoing filters may comprise pores and a size of the pores may decrease proceeding from the upper surface of the filter toward the lower surface of the filter.

Any of the foregoing filters may be configured to separate red blood cells from a sample of blood and to permit passage of liquid components of the sample of blood.

In any of the foregoing filters, the lower surface of the filter may be convex or tapered along at least one dimension. The lower surface of the filter may be convex or tapered along a dimension perpendicular to a dimension of the filter along which the lower surface of the filter contacts the surface of the substrate.

In any of the foregoing filters, a portion of the surface of the substrate may contact the central portion of the lower surface of the filter along a first dimension of the filter and along a second dimension of the filter and wherein the distance contacted along the first dimension of the filter may be at least about 5 times, e.g., at least about 7.5 times, e.g., at least about 10 times, greater than along the second dimension of the filter, and wherein the first and second dimensions may be perpendicular and further wherein the lower surface of the filter may be convex or tapered along the second dimension of the filter.

BRIEF DESCRIPTION OF THE DRAWINGS

FIG. 4b is a further close-up perspective cross-sectional view through a sample introduction zone of the microfluidic device of FIG. 1 taken along the cross section shown in FIG. 7 from the perspective of FIG. 4a.

FIG. 6b is a further close-up perspective cross-sectional view through a sample introduction zone of the microfluidic device of FIG. 1 taken along the cross section shown in FIG. 7 from the perspective of FIG. 6a.

FIG. 7 is identical with FIG. 1 except for showing the cross-sections of FIGS. 4a, 4b, 5, 6a, and 6b.

DETAILED DESCRIPTION OF THE INVENTION

Figure 1:
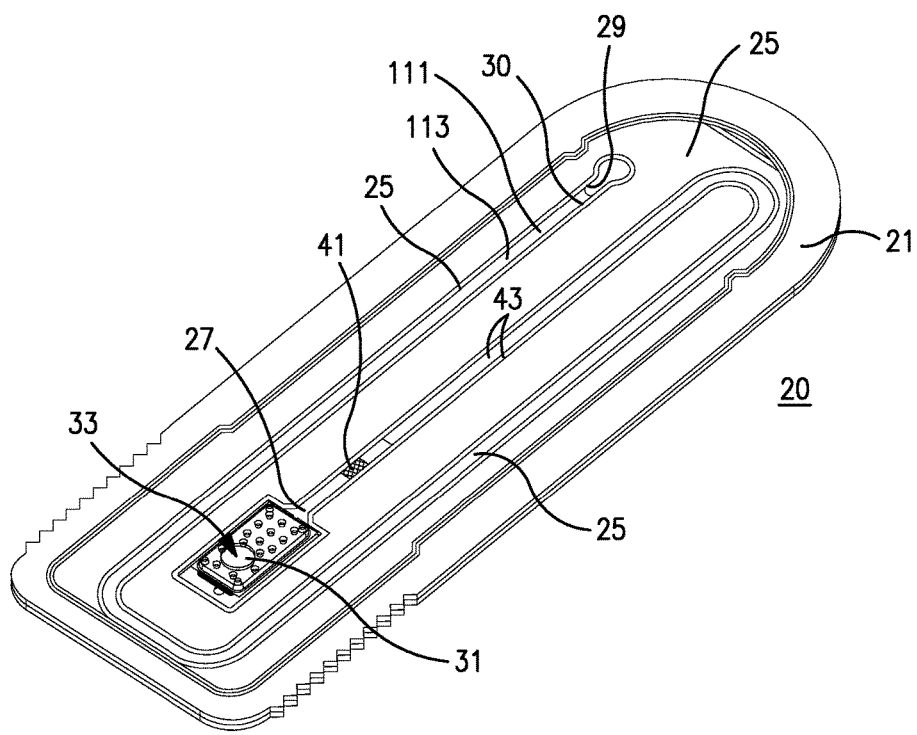
FIG. 1 is a perspective top view of a microfluidic device.

With reference to FIGS. 1-7, a microfluidic device 20 is configured to receive a liquid sample for the determination of one or more targets present in the liquid sample. Microfluidic device 20 is formed of a lower substrate 21 and an upper substrate 23 defining therebetween a capillary flow channel 25 having a proximal opening 27 and a vent 29 disposed adjacent a distal portion 30 of capillary channel 25. A reagent 41 and detection zone 43 are disposed within capillary flow channel 25. Microfluidic device 20 further includes a sample introduction port 31 through upper substrate 23. A liquid sample is introduced to microfluidic device via introduction port 31.

Filter 33 has an upper surface 35 and a lower surface 37 disposed between lower and upper substrates 21 and 23. Filter 35 is typically configured to receive a liquid sample, e.g., blood or urine, comprising particulates, e.g., cells, such as red or white blood cells, by application to upper surface 35 and to prepare a filtered liquid with a reduced number such particulates, e.g., essentially free of such particulates, through lower surface 37.

Figure 6A:
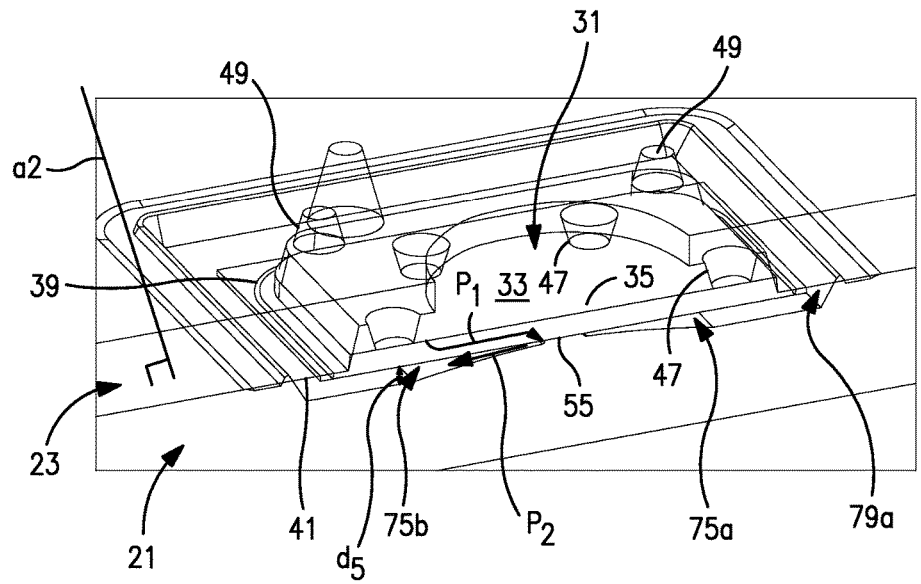
FIG. 6a is a close-up perspective cross-sectional view through a sample introduction zone of the microfluidic device of FIG. 1 taken along the cross section shown in FIG. 7.
Figure 6B:
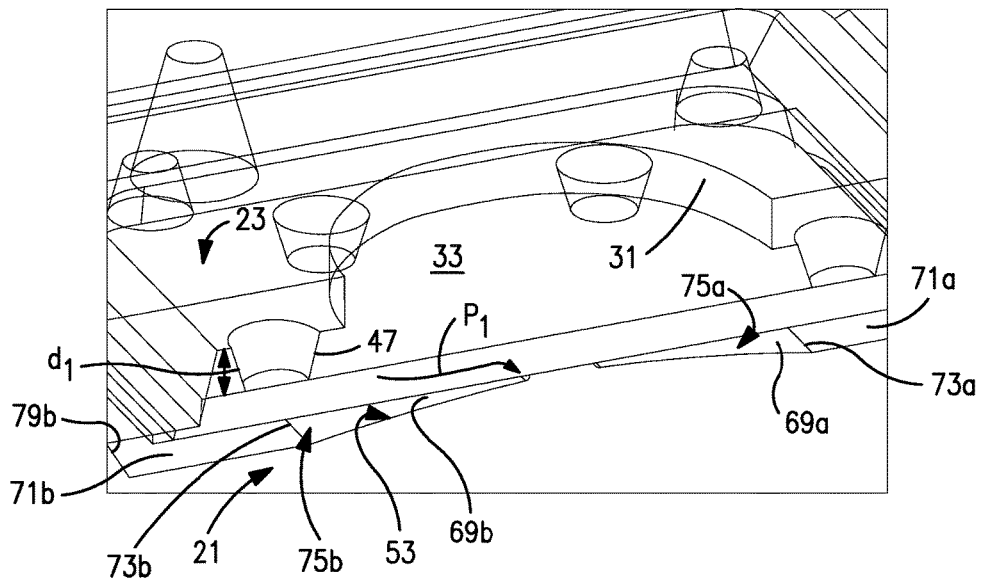
Figures 5, 6A, 6B, 7:
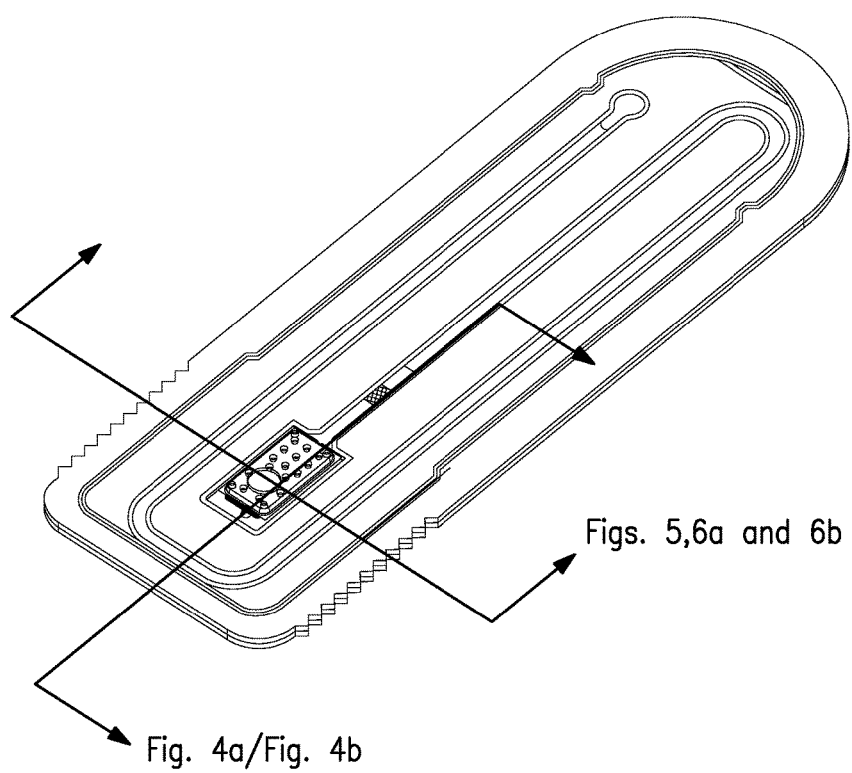
Figure 8:
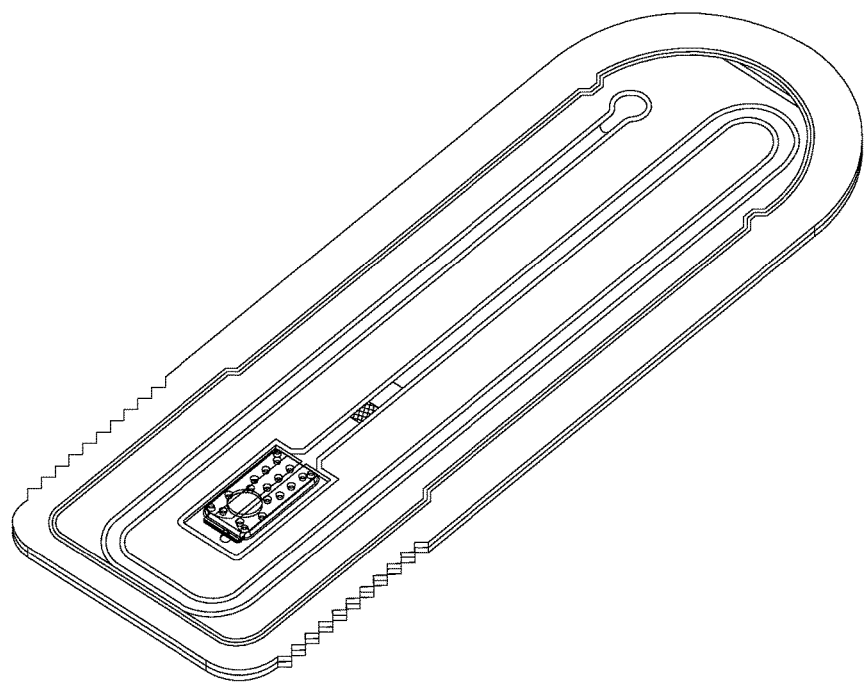
FIG. 8 is a perspective top view of the microfluidic device of FIG. 1 with a sample filter removed.
Figure 9:
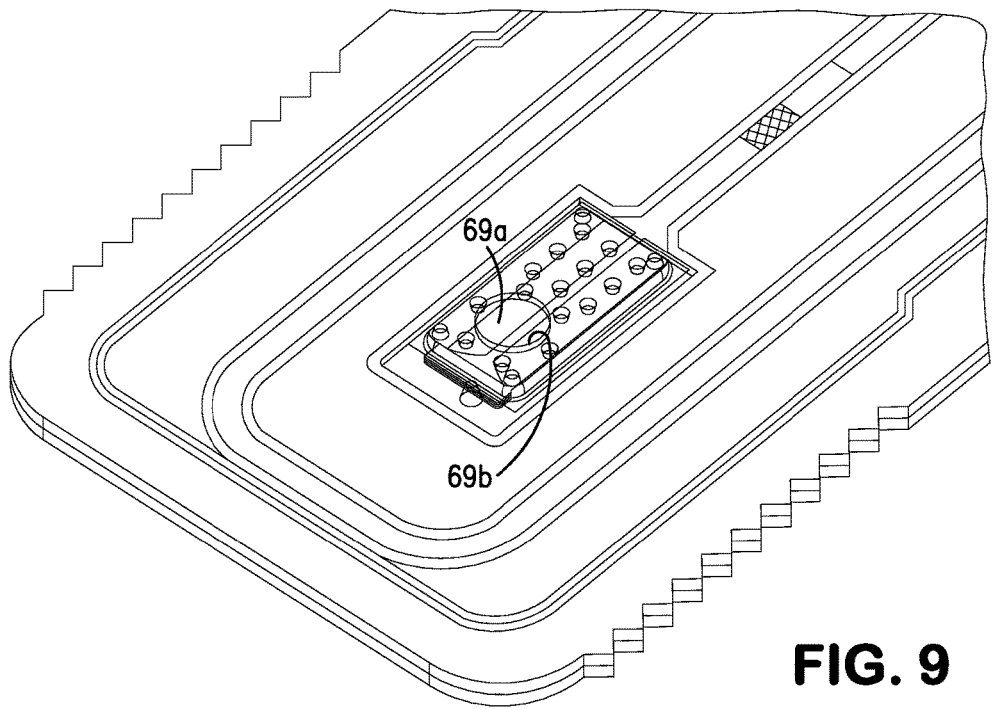
FIG. 9 is a close-up view of the microfluidic device of FIG. 1 with the sample filter removed as in FIG. 8.

In embodiments, filter 35 includes pores (not shown) having a size that decreases proceeding from upper surface 35 toward lower surface 37. The size variation of the pores is typically configured so that the particulates in a liquid sample applied to surface 35 pass into an interior of filter 33 but do not pass through second surface 37 of filter 33. In embodiments, filter 33 permits liquid sample passing from upper surface 35 to lower surface 37 to move laterally within filter 35, e.g., along a path p2 (FIGS. 4a and 4b) and/or a path p1 (FIGS. 6a and 6b). Such lateral movement permits liquid sample applied to filter 33 at upper surface 35 within port 31 to exit lower surface 37 of filter 33 at locations laterally spaced apart from port 31.

The filter may also be used to deliver one or more reagents to the liquid sample such as one or more buffers, one or more anti-coagulants, one or more salts, one or more stabilizers, one or more protein blockers protein, or combination of one or more such reagents. Additional or alternative reagents include reagents that reduce hemolysis of red blood cells in blood samples and reagents that improve the wettability of the filter with respect to aqueous samples.

Filter 33 has a length l1 and a width w1 (FIG. 2) sufficient to provide an area to accommodate a desired amount of sample applied to upper surface 35 thereof. For example, length l1 may be at least about 2.5 mm, at least about 5 mm, at least about 7.5 mm. Length l1 may be about 25 mm or less, about 20 mm or less, about 15 mm or less, about 10 mm or less. Width w1 may be at least about 2.5 mm, at least about 3.5 mm, at least about 5 mm. Width w1 may be about 17.5 mm or less, about 12.5 mm or less, about 10 mm or less, about 7.5 mm or less.

Figure 2:
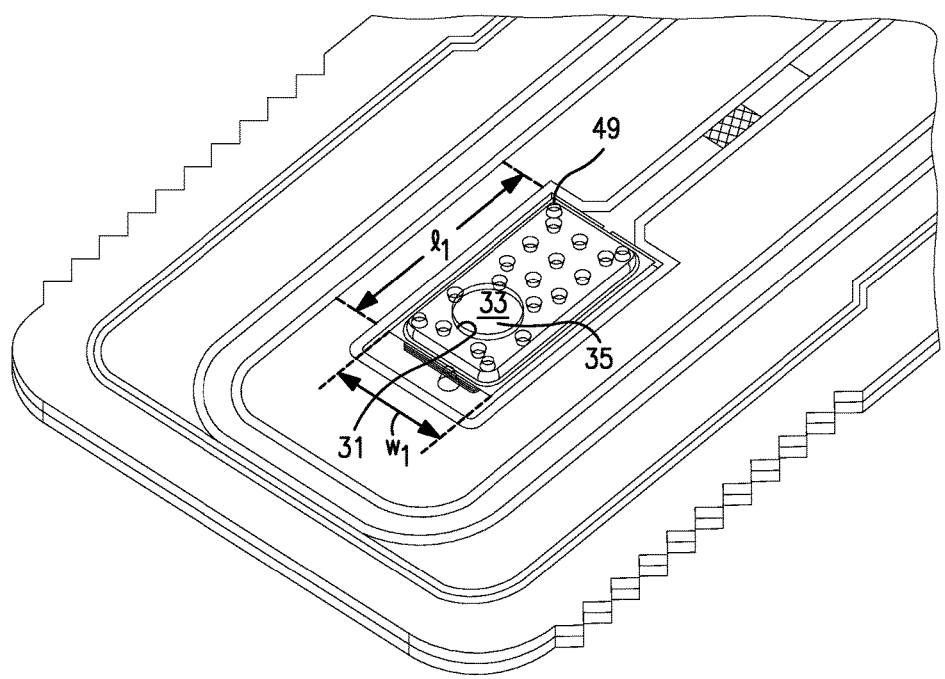
FIG. 2 is a close-up view of the microfluidic device of FIG. 1 from the perspective of FIG. 1.
Figure 3:
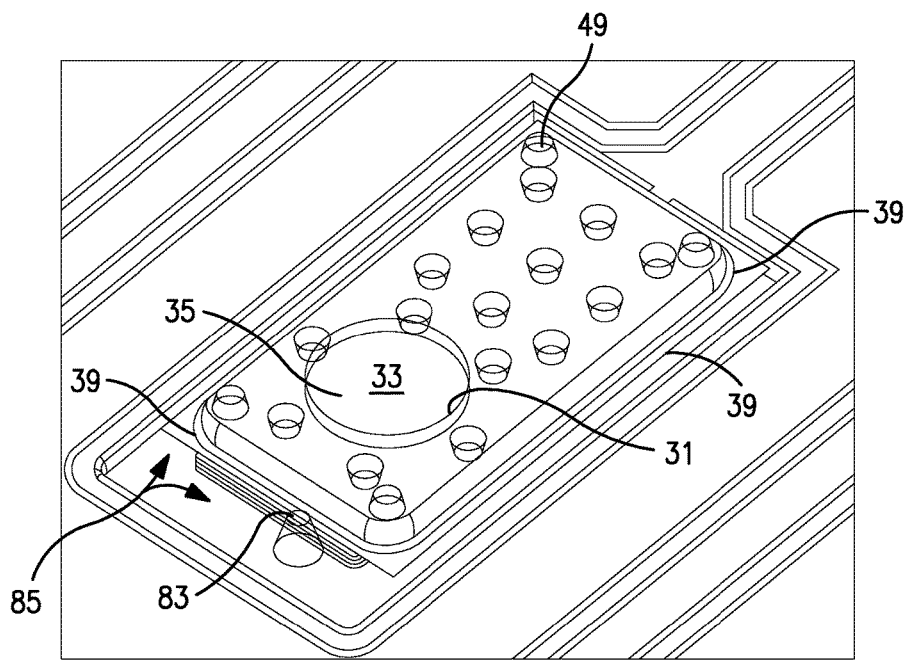
FIG. 3 is a further close-up view of the microfluidic device of FIG. 1 from the perspective of FIGS. 1 and 2.
Figure 13:
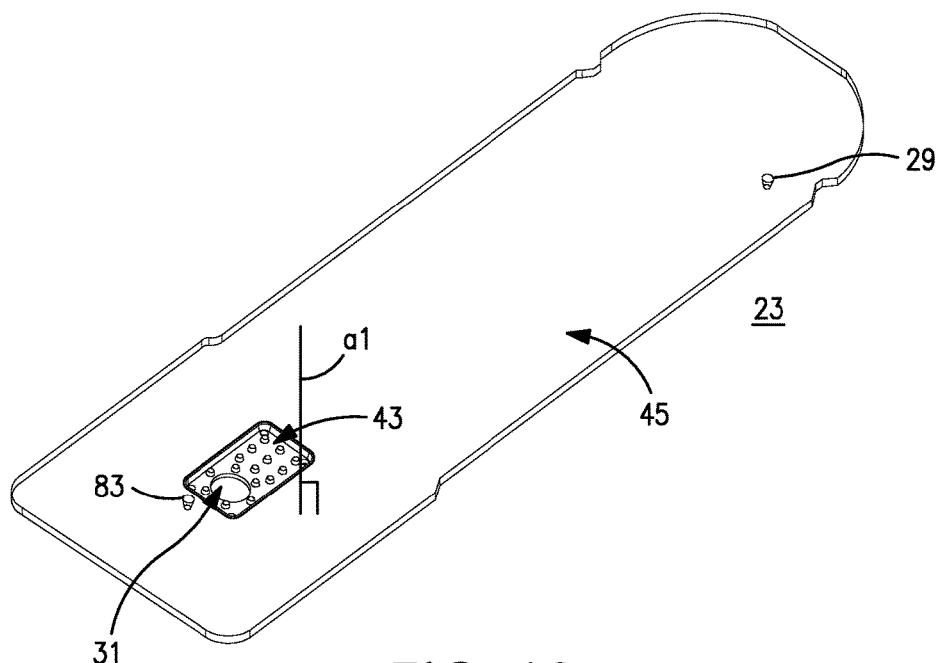
FIG. 13 is a perspective view of an underside of the upper substrate of the microfluidic device of FIG. 1.
Figure 14:
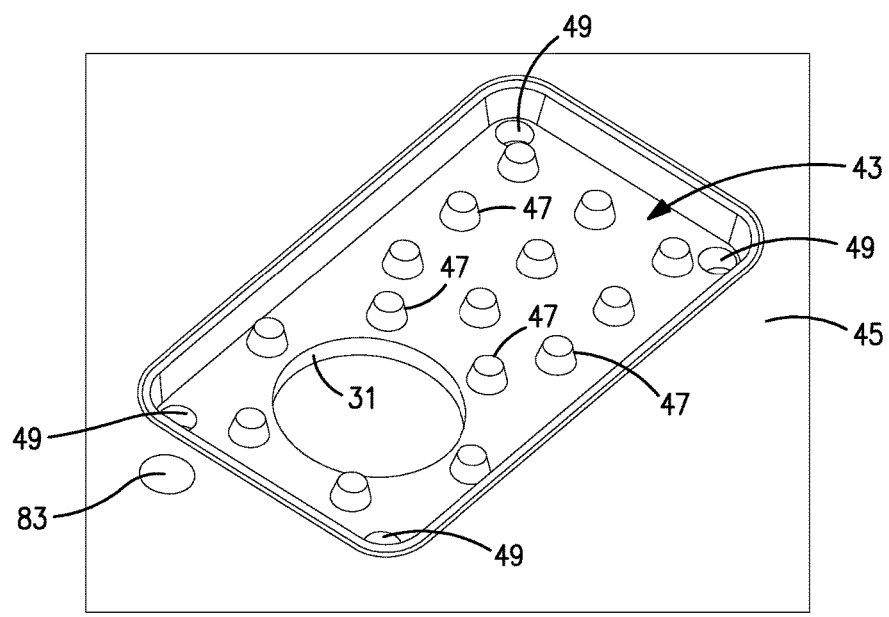
FIG. 14 is a close-up view of the underside of the upper substrate shown in FIG. 13.

Filter 33 is typically secured with respect to upper substrate 23. For example, a perimeter portion 39 of upper surface 35 of filter 33 may be attached, e.g., by heat staking, laser welding, or via an adhesive, to a lower surface 41 of upper substrate 23. In the embodiment of FIGS. 1-3, filter 33 is not attached to lower substrate 21, although such attachment may be used. Also with reference to FIGS. 13 and 14, a portion of filter 33, e.g., an upper portion of upper surface 35 disposed interior to perimeter 39, is accommodated within a recess 43 of a lower surface 45 of upper substrate 23. Recess 43 includes a plurality of projections 47 that project outwards from lower surface 45 of substrate 23 for a distance d1. Projections 47 contact upper surface 35 of filter 33 forming a cavity 51 having a height about the same as, e.g., the same as, distance d1. Typically, distance d1 is sufficient to permit a gas and/or liquid sample to flow between upper surface 35 of filter 33 and lower surface 45 of substrate 23. In embodiments, d1 may be at least about 5 microns, at least about 10 microns, at least about 15, microns, or at least about 25 microns. In embodiments, d1 is about 1000 microns or less, about 250 microns or less, about 175 microns or less, about 125 microns or less, or about 100 microns or less.

Recess 43 also includes a plurality of vents 49 that permit gas to pass between recess 43 and the ambient atmosphere (e.g., the atmosphere generally surrounding the microfluidic device) without passing through port 31. In use, liquid sample applied to filter 33 through port 31 travels laterally across surface 35 of filter 33 in gap 51 between surface 35 and surface 43 of upper substrate 23 while gas displaced by the advancing liquid escapes recess 43 via vents 49. Thus, sample applied to port 31 will contact an area of upper surface 35 of filter 33 that is larger than an area of port 31. This permits a more efficient use of filter 33 than if liquid applied to port 31 contacted an area of upper surface 35 limited to the area of port 31. In embodiments, a ratio of an area of upper surface 35 of filter 33 to an area of port 31 is at least about 1.5, at least about 2, or at least about 2.5. In embodiments, the ratio of the area of upper surface 35 of filter 33 to the area of port 31 is about 10 or less, about 7.5 or less, or about 5 or less. Typically, liquid sample applied to filter 33 through port 31 will contact at least about 50%, at least about 75%, at least about 80%, at least about 90%, or more of the area of upper surface 35 of filter 33.

With reference to FIGS. 4a, 4b, 5, 6a, 6b, and 10, an upper surface 53 of lower substrate 21 defines a filter contact surface 55 comprising a ridge 57 and a distal portion 59. A lower surface 37 of filter 33 contacts lower substrate 21 only at filter contact surface 55 (although in some embodiments, lower surface 37 may contact lower substrate 21 at locations other than filter contact surface 55).

Filter contact surface 55 contacts lower surface 37 of filter 33 only at locations of lower surface 37 that are disposed inwardly from perimeter 39 of filter. A distance between perimeter 39 and the nearest contact point of contact surface 55 may be at least about 250 microns, at least about 375 microns, at least about 500 microns, at least about 750 microns, or at least about 1 mm.

Figure 10:
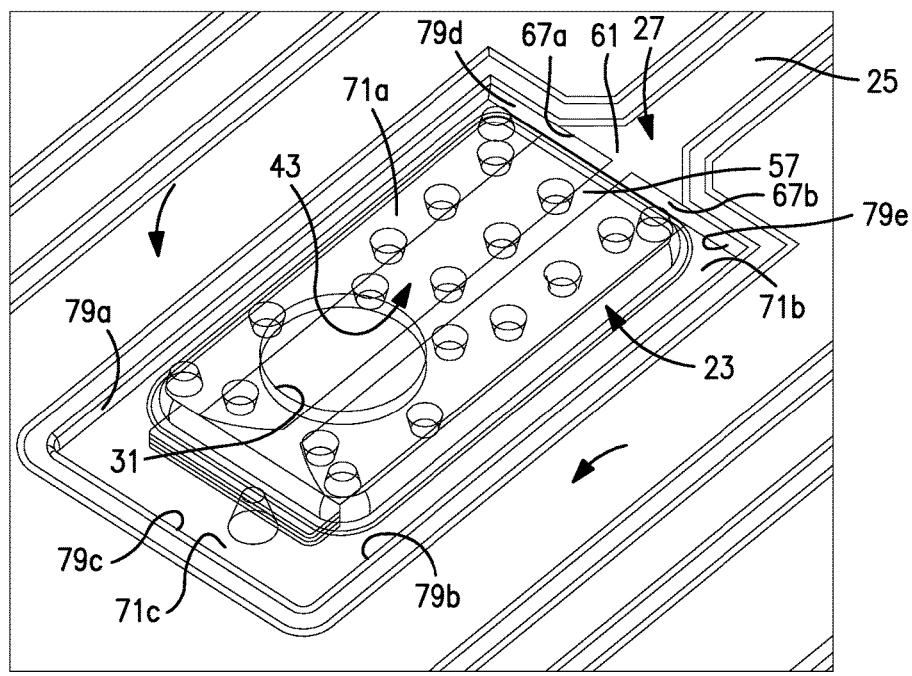
FIG. 10 is a further close-up view of the microfluidic device of FIG. 1 with the sample filter removed as in FIG. 8.

Ridge 57 extends proximally from a proximal floor 61 of proximal opening 27 of capillary channel 25 to distal portion 59 of filter contact surface 55 (FIG. 10). In embodiments, ridge 57 of filter contact surface 55 contacts lower surface 37 of filter 33 at one or more locations spaced apart along at least about 50%, at least about 70%, at least about 80%, at least about 90%, at least about 95%, e.g., substantially all of length l1 of filter 33. For example, ridge 57 of filter contact surface 55 may contact lower surface 37 of filter 33 continuously (i.e., without gaps) along at least about 50%, at least about 70%, at least about 80%, at least about 90%, at least about 95%, e.g., substantially all of length l1 of filter 33. In embodiments, a length l2 of ridge 57 of filter contact surface 55 is at least about 5 mm, at least about 7.5 mm, at least about 10 mm. Length l2 may be about 25 mm or less, about 20 mm or less, or about 15 mm or less.

In embodiments, ridge 57 of filter contact surface 55 contacts lower surface 37 of filter 33 at one or more locations spaced apart along about 50% or less, about 30% or less, about 25% or less, about 20% or less, about 15% or less, or about 10% or less of width w1 of filter 33. In embodiments, ridge 57 of filter contact surface 55 has a width w2 (FIG. 12) of at least about 100 microns, at least about 200 microns, at least about 300 microns, at least about 500 microns. Width w2 of filter contact surface 55 may be about 1000 microns or less, about 750 microns or less, about 650 microns or less, or about 500 microns or less. In embodiments, length l2 of ridge 57 is at least about 5 times greater, at least about 7.5 times greater, at least about 10 times greater, at least about 15 times greater than width w2 of ridge 57 where length l2 and width w2 are taken along perpendicular dimensions of ridge 57.

Figure 12:
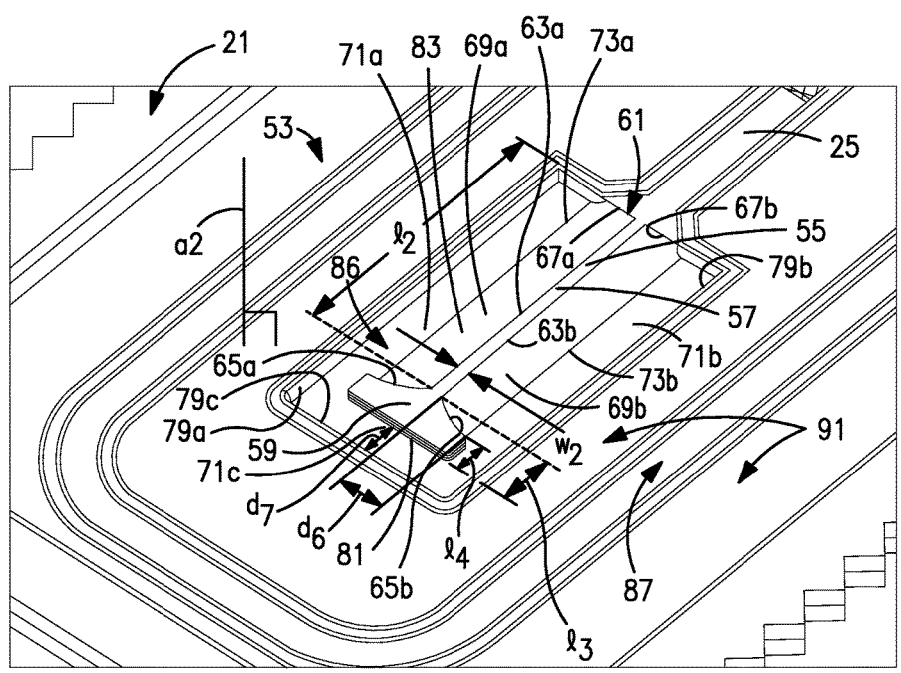
FIG. 12 is a close up view of the microfluidic device of FIG. 1 with the sample filter and upper substrate removed as in FIG. 11.

A maximum length l3 of distal portion 59 of filter contact surface 55 is typically less than length l2 of ridge 57 of filter contact surface 55 (FIG. 12). For example, a ratio of l3 and l3 may be about 0.5 or less, about 0.35 or less, about 0.25 or less, about 0.2 or less, or about 17.5 or less. A minimum length l4 of distal portion 59 of filter contact surface 55 is typically less than length l3 (FIG. 12). For example, a ratio of length l4 and l3 may be about 0.95 or less, about 0.9 or less, about 0.8 or less.

Ridge 57 of filter contact surface 55 defines first and second opposed walls 63a,63b and distal portion 59 of filter contact surface 55 defines first and second distal walls 65a,65b. Proximal portion 61 of capillary channel 25 defines first and second proximal walls 67a,67b. Upper surface 53 of lower substrate 21 defines first and second sloping floor portions 69a,69b and first, second and third hydrophobic floor portions 71a,71b,71c. First and second sloping floor portions 69a,69b and first and second hydrophobic floor portions 71a,71b are respectively separated by first and second junctions 73a,73b. A third hydrophobic floor portion 71c is disposed distal to a distal wall 81 extending downward from filter contact surface 59.

As seen, for example, in FIGS. 10 and 12, peripheral portions of first, second, and third hydrophobic floor portions 71a,71b,71c abut peripheral walls 79a,79b,79c,79e that extend upward to define a perimeter of a recess 81 in upper surface 53 of lower substrate 23. Capillary contact surface 55 and first and second proximal floor portions 69a,69b constitute a projection extending above first, second, and third hydrophobic floor portions 71a,71b,71c within recess 81.

Figure 4A:
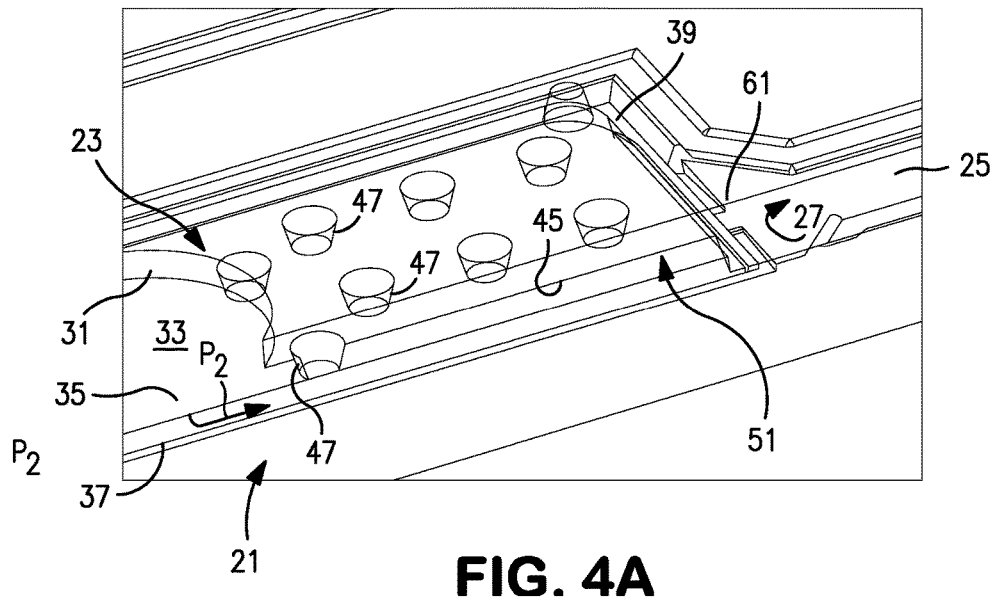
FIG. 4a is a close-up perspective cross-sectional view through a sample introduction zone of the microfluidic device of FIG. 1 taken along the cross section shown in FIG. 7.
Figure 4B:
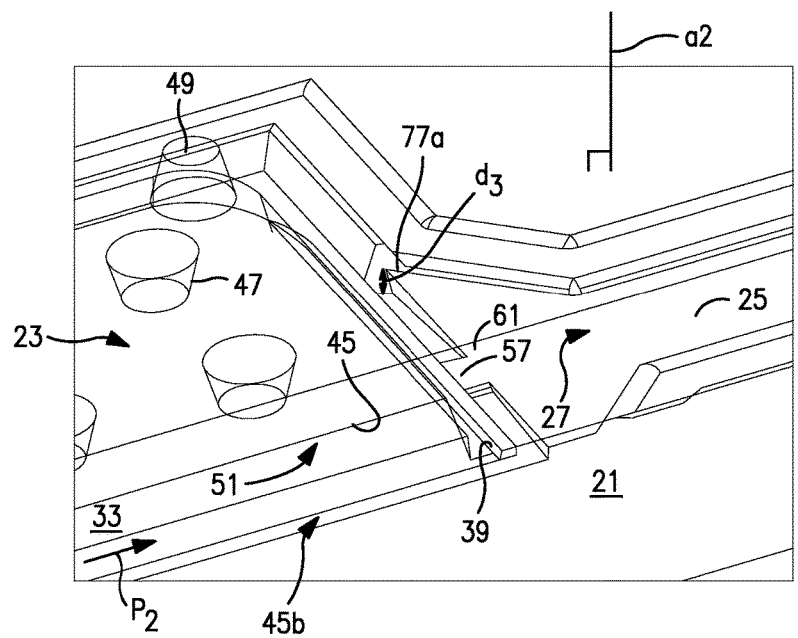
Figure 5:
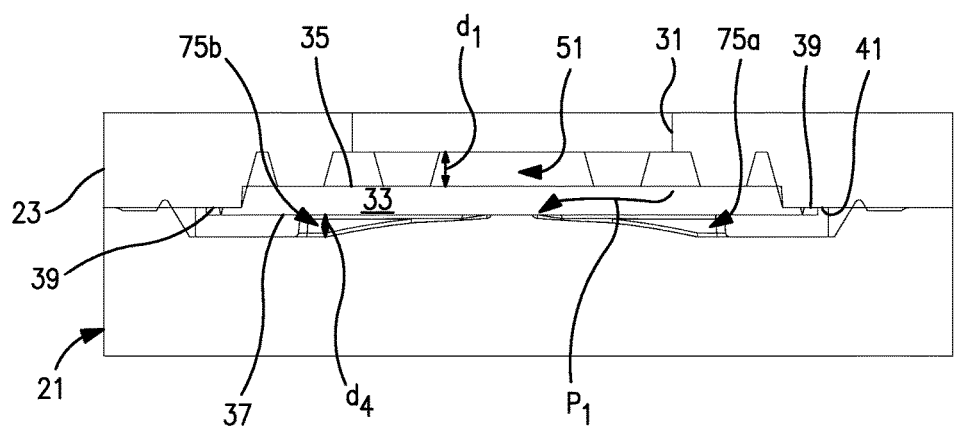
FIG. 5 is a cross-sectional view through the sample introduction zone of the microfluidic device of FIG. 1 taken along the cross section shown in FIG. 7.

Taken together, first and second opposed walls 63a,63b, first and second distal walls 65a,65b, first and second proximal walls 67a,67b, first and second junctions 73a,73b, first and second sloping floor portions 69a,690b, and portions of lower surface 37 above first and second sloping floor portions 69a,690b, and portions of lower surface 37 below first and second sloping floor portions 69a,690b define respective sample cavities 75a,75b. With reference to FIGS. 4b,6a and 12, sample cavities 75a,75b are spaced apart from, e.g., disposed below, a level of floor 61 of capillary channel 25 along an axis a2 oriented normal to lower substrate 21. In embodiments, at least about 50%, at least about 75%, at least about 85%, at least about 95%, essentially all of a volume of cavities 75a,75b is disposed below floor 61 of the proximal portion of capillary channel 25 along axis a2. In embodiments, at least about 50%, at least about 75%, at least about 85%, at least about 95%, or essentially all of an active area of lower surface 37 of filter 33 is disposed at or below floor 61 of the proximal portion of capillary channel 25 along axis a2. In embodiments, at least about 50%, at least about 75%, at least about 85%, at least about 95%, essentially all of a volume of cavities 75a,75b is disposed at or at a greater distance along axis a2 from an upper surface of upper substrate 23 than floor 61 of the proximal portion of capillary channel 25. In embodiments, at least about 50%, at least about 75%, at least about 85%, at least about 95%, or essentially all of an active area of lower surface 37 of filter 33 is disposed at or at a greater distance along axis a2 from an upper surface of upper substrate 23 than floor 61 of the proximal portion of capillary channel 25. An active area of filter 33 is the area through which filtered liquid emerges during use.

Taken together, first, second, and third hydrophobic floor portions 71a,71b,71c, portions of lower surface 37 of filter 33 above and first, second, and third hydrophobic floor portions 71a,71b,71c peripheral walls 79a,79b,79c,79e define a peripheral cavity 85 in gaseous communication with sample cavities 75a,75b. A vent 83 permits gas to pass between on the one hand active cavities 75a,75b and peripheral cavity 85 and, on the other hand, the ambient atmosphere (e.g., the atmosphere generally surrounding the microfluidic device) without passing through filter 33. Vent 83 is disposed distal of active cavities 75a,75b.

A height d2 of first and second opposed walls 63a,63b is typically at least about 10 microns, at least about 20 microns, at least about 30 microns, at least about 50 microns, at least about 75 microns, at least about 100 microns, or at least about 150 microns. Height d2 may be about 175 microns or less, about 125 microns or less, about 100 microns or less, about 75 microns or less, or about 50 microns or less. Typically, height d2 of first and second opposed walls 63a,63b is about the same as, e.g., the same, as the height of first and second proximal walls 67a,67b immediately adjacent ridge 57 and proximal portion 61 of capillary channel 25. In embodiments, height d2 is zero so that first and second sloping floor portions 69a,69b slope downwards from ridge 57 of filter contact surface 55.

Because first and second sloping floor portions 69a,69b slope away from lower surface 37 of filter 33 proceeding laterally away from ridge 57, the height of first and second proximal walls 67a,67b increases from a minimum immediately adjacent ridge 57 and proximal portion 61 of capillary channel 25 to a maximum height d3 at lateral portions 77a,77b of first and second proximal walls 67a,67b. Height d3 of lateral portions 77a,77b of first and second proximal walls 67a,67b is typically at least about 30 microns, at least about 50 microns, at least about 75 microns, at least about 100 microns, at least about 150 microns, at least about 200 microns, or at least about 250 microns. Height d3 may be about 500 microns or less, about 350 microns or less, about 300 microns or less, about 275 microns or less, or about 225 microns or less. First and second sloping floor portions 69a,69b have a convex shape in at least one dimension, e.g., are cylindrically convex about an axis extending between first and second proximal walls 67a,67b and first and second distal walls 65a,65b. In embodiments, first and second sloping floor portions 69a,69b are planar or arcuate.

A height of first and second distal walls 65a,65b, i.e., the distance between distal portion 59 of filter contact surface 55 and first and second sloping floor portions 69a,69b, is typically about the same as the height of first and second proximal walls 67a,67b, which, as discussed above, increases from a minimum immediately adjacent ridge 57 and proximal portion 61 of capillary channel 25 to a maximum height d3 at lateral portions 77a,77b of first and second proximal walls 67a,67b.

A height d4 of a gap between first and second junctions 73a,73b of upper surface 53 of lower substrate 21 and lower surface 37 of filter 33 (FIG. 5) is typically at least as large as, e.g., larger than, height d3 at lateral portions 77a,77b of first and second proximal walls 67a,67b. Height d4 is typically at least about 30 microns, at least about 50 microns, at least about 75 microns, at least about 100 microns, at least about 150 microns, at least about 200 microns, or at least about 250 microns. Height d4 may be about 600 microns or less, about 400 microns or less, about 350 microns or less, about 300 microns or less, or about 275 microns or less. A height d5 between first and second hydrophobic floor portions 71a,71b of upper surface 53 of lower substrate 21 and lower surface 37 of filter 33 (FIG. 6a) may be about the same as, e.g., the same as, height d4. Height d5 is typically constant (but may also vary) proceeding laterally from first and second junctions 73a,73b of upper surface 53 of lower substrate 21 toward first and second lateral walls 79a,79b (FIGS. 6a, 6b, and 12).

A lateral distance d6 (FIG. 12) between first and second opposed walls 63a,63b and first and second junctions 73a, 73b is typically at least about 1 mm, at least about 1.25 mm, at least about 1.5 mm, at least about 1.75 mm, or at least about 2 mm. Lateral distance d6 may be about 10 mm or less, about 7.5 mm or less, about 5 mm or less, about 3 mm or less, or about 2.5 mm or less. A distance d7 (FIG. 12)

between distal wall 79c and a distal wall 81 is typically about the same as, e.g., the same, as distance d6.

Figure 11:
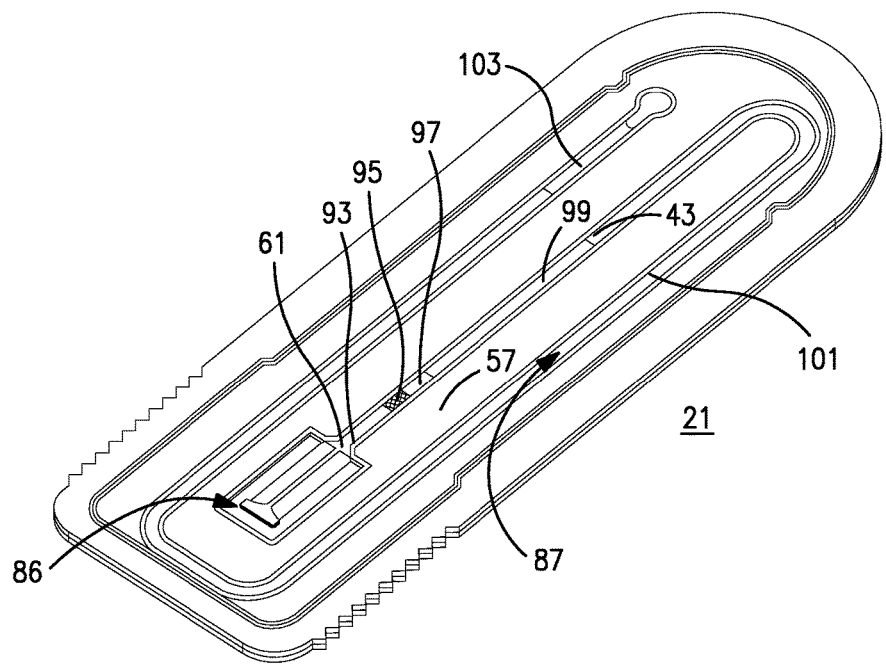
FIG. 11 is a perspective top view of the microfluidic device of FIG. 1 with the sample filter removed and with an upper substrate removed.

With reference to, for example, FIGS. 11 and 12, peripheral walls 79a,79b,79c,79e define a periphery of a recess 86 in a surface 53 of lower substrate 21. First, second, and third hydrophobic floor portions 71a,71b,71c and first and second sloping floor portions 69a,69b define a floor of recess 86. First, second, and third hydrophobic floor portions 71a,71b, 71c and first and second sloping floor portions 69a,69b are spaced apart from, e.g., below, portions of upper surface 53 of lower substrate 21 adjacent to recess 86 along an axis a2 normal to upper surface 53 and/or along an axis a1 normal to lower surface 45 of upper substrate 23 (FIG. 13) when upper substrate is secured with respect to lower substrate 21. In embodiments, at least about 50%, at least about 75%, at least about 90%, at least about 95%, or essentially all of the area of first, second, and third hydrophobic floor portions 71a,71b,71c and first and second sloping floor portions 69a,69b are spaced apart from, e.g., below, portions of upper surface 53 of lower substrate 21 adjacent to recess 86.

Upper surface 53 of lower substrate 21 further defines a groove 87 extending from a proximal portion 93 (same as proximal floor 61), a reagent portion 95, a ramp portion 97, a detection portion 99, and a distal portion 101. First, second, and third hydrophobic floor portions 71a,71b,71c and first and second sloping floor portions 69a,69b are spaced apart from, e.g., below, groove 87. In embodiments, at least about 50%, at least about 75%, at least about 90%, at least about 95%, or essentially all of the area of first, second, and third hydrophobic floor portions 71a,71b,71c and first and second sloping floor portions 69a,69b are spaced apart from, e.g., below, at least a portion of groove 87, e.g., at least 50%, at least about 75%, at least about 90%, essentially all of groove 87. In embodiments, at least about 50%, at least about 75%, at least about 90%, at least about 95%, or essentially all of the area of first, second, and third hydrophobic floor portions 71a,71b,71c and first and second sloping floor portions 69a,69b are spaced apart from, e.g., below, at least a portion of groove 87 disposed proximal to detection zone 43, e.g., at least 50%, at least about 75%, at least about 90%, essentially all of groove 87 disposed proximal to detection zone 43.

Channel 25 has a width of about 900 microns between reagent portion 95 and distal portion 101. In embodiments, the width of channel 25 is at least about 500 microns, at least about 750 microns, at least about 850 microns. The width of channel 25 may be about 2500 microns or less, about 2100 microns or less, or about 1750 microns or less.

Detection zone 43 of microfluidic device 20 typically includes a one or more capture zones. A capture zones is comprised of reagents, such as receptors, or devices, such as electrodes which bind or react with one or more components from the liquid sample and/or reagents combined with the liquid sample. Such binding or reaction is related to the presence or amount of target ligand in the sample. One or more detection zones 43 can be placed in the capillary channel 25 to measure the presence or amount of one or more target ligands. Reagent portion 95 of microfluidic device 20 includes one or more reagents that facilitate detection of one or more targets in a liquid sample. Exemplary reagents and techniques for depositing such reagents in reagent portion 95 are described in U.S. Pat. No. 7,824,611, which is incorporated herein by reference.

For example, as described in U.S. Pat. No. 7,824,611, texture on a device surface can facilitate drying of reagents on the surface during preparation of the device, as well as uniform placement of dried reagents on the surface as follows. A liquid reagent-containing fluid is placed in contact with the textured surface, and small reagent fluid menisci form adjacent each texture structure. Absent the presence of texture, the fluid would tend to form larger menisci at corners of the entire chamber, which when dried would produce a non-uniform layer of dried reagent. When texture structures are designed into the device, the presence of numerous small menisci leads to a more uniform layer of reagent that is dried throughout the chamber.

In embodiments, reagents, includes receptors which bind or react with one or more components from the liquid sample and/or reagents combined with the liquid sample. The reagents, such as receptors, may be immobilized on the surface of the device through covalent bonds or through adsorption. One embodiment is to immobilize receptor coated latex particles, for example of diameters ranging from about 0.1 µm to 5 µm. In addition, particles termed "nanoparticles" can also be coated with receptor and the resulting nanoparticles can be immobilized to the device through adsorption or covalent bonds. Nanoparticles are generally composed of silica, zirconia, alumina, titania, ceria, metal sols, and polystyrene and the like and the particle sizes range from about 1 nm to 100 nm. The benefit of using nanoparticles is that the surface area of the protein coating the nanoparticle as a function of the solids content is dramatically enhanced relative to larger latex particles. In one embodiment, the receptors bind to the surface through electrostatic, hydrogen bonding and/or hydrophobic interactions. Electrostatic, hydrogen bonding and hydrophobic interactions are discussed, for example, in Biochemistry 20, 3096 (1981) and Biochemistry 29, 7133 (1990). For example, the surface can be treated with a plasma to generate carboxylic acid groups on the surface. The receptor coated latex particles are preferably applied in a low salt solution, for example, 1-20 mM, and at a pH which is below the isoelectric point of the receptor. Thus, the negative character of the carboxylic acid groups and the positive charge character of the receptor latex will result in enhanced electrostatic stabilization of the latex on the surface. Hydrogen bonding and hydrophobic interactions would also presumably contribute to the stabilization and binding of the receptor latex to the surface. Magnetic fields may also be used to immobilize particles which are attracted by the magnetic field.

As discussed above, textured surfaces can serve to provide additional surface area which allows for a higher density of assay reagents to be immobilized thereon. Furthermore, a textured surface, or other surface modifications, can be provided to affect the flow characteristics of a fluid on or within the surface. For example, as disclosed herein a surface can be provided with hydrophobic regions to diminish the extent of fluid flow in the hydrophobic region, textures can be used that provide for a more uniform distribution of dried reagents on the surface, textures can be provided to modify the configuration of the meniscus at the fluid flow front, or textures can be used that provide the capillary driving force for movement of fluid within the surface.

Reagents include signal producing reagents. Such reagent include for example, a receptor specific for a target ligand adsorbed to a colloidal metal, such as a gold or selenium sol. Other reagents include ligand analogue-ligand complement conjugates to each target ligand and receptors adsorbed to latex particles with diameters of, for example, 0.1 µm to 5 µm to each target ligand, in appropriate amounts, for example, as taught by U.S. Pat. Nos. 5,028,535 and 5,089,391. The ligand complement on the conjugate can be any chemical or biochemical which does not bind to the receptors for the target ligands. Additional reagents include detergents for a washing step.

As used herein a target ligand refers to the binding partner to one or more receptors. Synonyms for target ligand are analyte, ligand or target analyte.

As used herein in a ligand refers to the binding partner to one or more ligand receptor(s). A synonym for ligand is analyte. For example, a ligand can comprise an antigen, a nucleotide sequence, lectin or avidin.

As used herein a ligand analogue refers to a chemical derivative of the target ligand which may be attached either covalently or noncovalently to other species, for example, to the signal development element. Ligand analogue and target ligand may be the same and both generally are capable of binding to the ligand receptor. Synonyms for ligand analogue are analyte analogue or target analyte analogue.

As used herein a ligand analogue conjugate refers to a conjugate of a ligand analogue and a signal development element. A ligand analogue conjugate can be referred to as a labeled ligand analogue.

As used herein a receptor refers to a chemical or biochemical species capable of reacting with or binding to target ligand, typically an antibody, a binding fragment, a complementary nucleotide sequence, carbohydrate, biotin or a chelate, but which may be a ligand if the assay is designed to detect a target ligand which is a receptor. Receptors may also include enzymes or chemical reagents that specifically react with the target ligand. A receptor can be referred to as a reagent or a binding member. A receptor which is neither a labeled receptor nor an immobilized receptor can be referred to as an ancillary receptor or an ancillary binding member. For example, a receptor can comprise an antibody.

As used herein a ligand receptor conjugate refers to a conjugate of a ligand receptor and a signal development element; synonyms for this term include binding member conjugate, reagent conjugate, labeled reagent or labeled binding member.

As used herein a ligand complement refers to a specialized ligand used in labeling ligand analogue conjugates, receptors, ligand analogue constructs or signal development elements.

As used herein a ligand complement receptor refers to a receptor for ligand complement and a ligand analogue-ligand complement conjugate refers to a conjugate including a ligand analogue and a ligand complement.

Ramp portion 97 of microfluidic device has a length along capillary channel 25 of 3 mm and a pitch of 14 microns per mm proceeding distally along capillary channel 25. The positive pitch decreases a height of capillary channel 25 from 75 microns prior to ramp portion 97 to 33 microns distal to ramp portion 97. In embodiments, a ramp portion may have a length of at least about 0.5 mm, at least about 1 mm, at least about 1.5 mm. A ramp portion may have a length of about 5 mm or less, about 4 mm or less, about 3.5 mm or less, about 3 mm or less, about 2 mm or less, about 1.5 mm or less. In embodiments, a pitch of the ramp portion may be at least about 10 microns per mm, at least about 12 microns per mm, at least about 14 microns per mm at least about 17.5 microns per mm. The pitch of the ramp portion may be about 30 microns per mm or less, about 25 microns per mm or less, about 20 microns per mm or less. In embodiments, the ramp portion is about 1 mm long with a pitch of 22 microns per mm proceeding distally along capillary channel 25 and decreases the height of the channel from about 55 microns proximal of the ramp portion to about 33 microns distal to the ramp portion.

In use, microfluidic device 20 is typically first removed from a sealed packaging material in which the device has been transported and/or stored. The packaging material is typically formed of a material that is resistant to an exchange of gas from an interior of the packaging material to the ambient gas surrounding the packaging material. After removal from the packaging, the microfluidic device is inserted into a reader (not shown) configured to operate microfluidic device 20 to detect one or more targets in a liquid sample, e.g., a blood or urine sample.

In embodiments, the liquid sample is a blood sample, e.g., a blood sample obtained from a finger of a human being. The liquid sample may have a total volume of about 75 microliters or less, 50 microliters or less, 30 microliters or less, 20 microliters or less, such as about 15 microliters or less, such as about 10 microliters or less. The liquid sample may be combined with reagent, e.g., a liquid and/or a dry reagent, prior to introducing the liquid sample to the microfluidic device.

With reference to FIGS. 15-19, the reader includes a syringe pump 101 that makes a fluidic connection, e.g., a gas-tight seal, with respect to distal vent 29 of capillary channel 25 of microfluidic device 20.

Liquid sample is then applied to upper surface 35 of filter 33 via port 31. Filtered liquid (e.g., liquid that emerges from lower surface 37 of filter 33 after being applied to upper surface 35 within port 31) passes into first and second cavity portions sample cavities 75a,75b. A high capillarity experienced by filtered liquid at first and second where lower surface 37 of filter contacts first and second opposed walls 63a,63b draws liquid out of filter 33 and into sample cavities 75a,75b, e.g., generally along path p2 and a path p3. First and second hydrophobic floor portions 71a,71b,71c prevent filtered liquid from passing beyond first and second junctions 73a,73b and into peripheral cavity 85.

Filtered liquid moves within sample cavities 75a,75b by capillary action to proximal opening 27 of capillary channel 25 and moves by capillary action at least a portion of the way into capillary channel 25. With the pump in fluidic connection with distal vent 29 of capillary channel 25, a volume of gas acting upon a distal gas-liquid interface 107 of the filtered liquid is confined within a volume determined by the volume of capillary channel 25 distal to interface 107 and a dead volume of the pump. As distal gas-liquid interface 107 moves distally along channel 25, the volume of the confined gas decreases and the pressure of the confined gas acting upon the distal gas-liquid interface 107 increases by an amount corresponding to decreased volume. The total volume of gas confined distal to opening 27 of capillary channel 25 is about 25 microliters. By total volume of gas it is meant a volume including the volume of gas in channel 25 and the volume of gas within pump 101 in communication with channel 25. In embodiments, the total volume of gas is about 50 microliters or less, about 35 microliters or less, about 30 microliters or less, or about 25 microliters or less. The total volume of gas may be at least about 10 microliters, at least about 15 microliters, at least about 20 microliters. The volume of channel 25 is typically at least about 7.5 microliters, at least about 10 microliters, or at least about 12.5 microliters. The volume of channel 25 may be about 25 microliters or less, about 20 microliters or less, about 17.5 microliters or less, or about 15 microliters or less.

Figure 15:
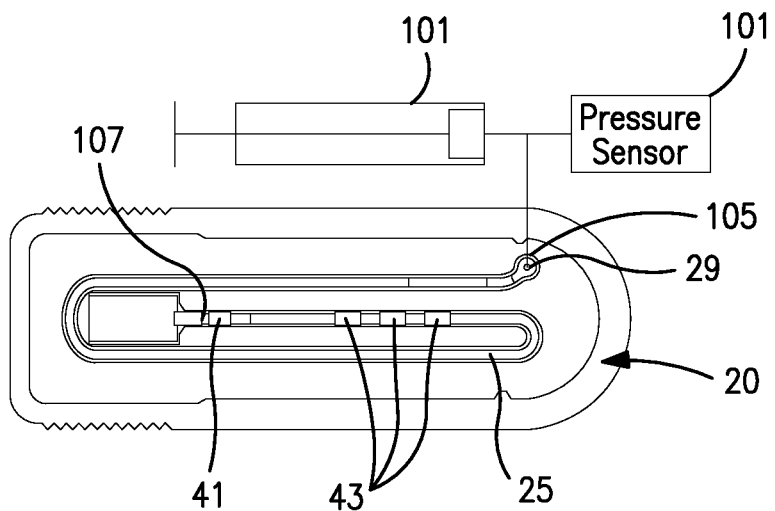
FIG. 15 is a top view of the microfluidic device of FIG. 1 in a first state following the introduction of a liquid sample but with the top substrate having been removed as in FIG. 5 and further showing a pump and pressure sensor.

Before distal gas liquid interface 107 of the filtered liquid contacts reagent portion 41 of capillary channel 25 the gas pressure acting on distal gas liquid interface 107 increases such that the capillary force experienced by the filtered liquid is insufficient to move the filtered liquid further along the capillary channel (FIG. 15).

The pressure of the gas acting upon the distal gas liquid interface of the filtered liquid is determined using a pressure sensor 103 in communication with the volume of gas enclosed distal to distal gas-liquid interface 107. Pressure sensor 103 may be configured to determine an absolute pressure of the enclosed gas, e.g., a pressure with respect to a pressure of ambient gas, e.g., a pressure of gas acting upon outer surfaces of microfluidic device 20.

Figure 16:
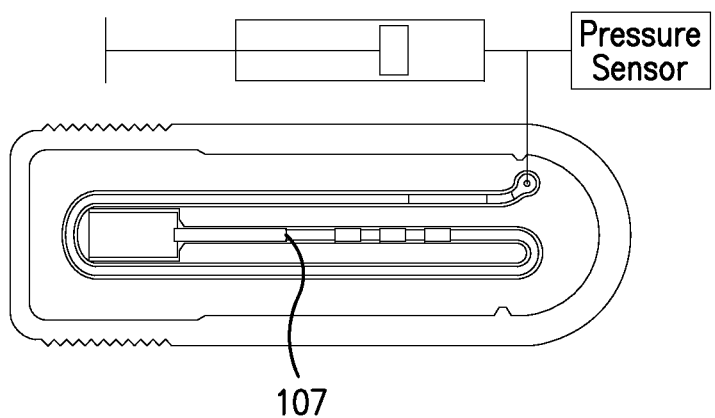
FIG. 16 shows the microfluidic device of FIG. 15 in a second state following the introduction of a liquid sample.

The reader actuates syringe pump 101 to increase a volume of the enclosed gas by an amount sufficient to decrease the gas pressure acting on distal gas-liquid interface 107. Capillary action draws the filtered liquid further along capillary channel 107 until distal gas liquid interface 107 contacts and then passes beyond reagent portion 41. A gas pressure acting on distal gas liquid interface 107 increases such that the capillary force experienced by the filtered liquid is insufficient to move the filtered liquid further along the capillary channel (FIG. 16).

Figure 17:
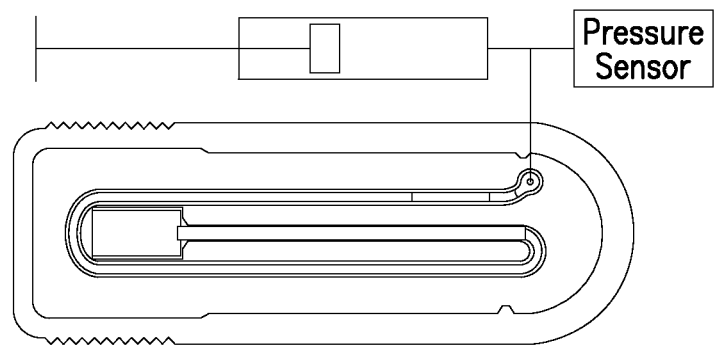
FIG. 17 shows the microfluidic device of FIG. 15 in a third state following the introduction of a liquid sample.

After a period of time sufficient to permit the filtered liquid and reagent to react and/or combine with a reagent in reagent portion 41, the reader actuates syringe pump 101 to increase the volume of the enclosed gas by an amount sufficient to decrease the gas pressure acting on distal gas-liquid interface 107. Capillary action draws the filtered liquid further along capillary channel 107 until distal gas liquid interface 107 contacts and then passes beyond detection zone 42. A gas pressure acting on distal gas liquid interface 107 increases such that the capillary force experienced by the filtered liquid is insufficient to move the filtered liquid further along the capillary channel (FIG. 17).

Figure 18:
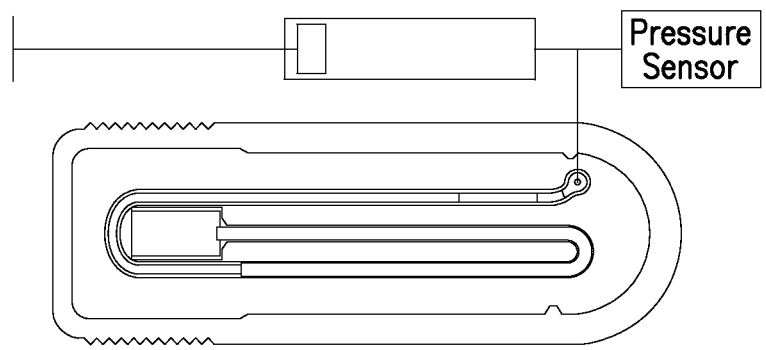
FIG. 18 shows the microfluidic device of FIG. 15 in a fourth state following the introduction of a liquid sample.

Reagent and target (if any) combine and/or react with detection zone 43, e.g., by binding a detectable label to a binding agent present in detection zone 43. After a period of time sufficient to permit the filtered liquid and reagent to react and/or combine with detection zone 43, the reader actuates syringe pump 101 to increase the volume of the enclosed gas by an amount sufficient to decrease the gas pressure acting on distal gas-liquid interface 107. Capillary action draws the filtered liquid further along capillary channel 107 until substantially all reagent from reagent zone 43 that has not bound to detection zone 43 has moved distal of detection zone 43 along capillary channel 25 (FIG. 18). The pump may be actuated to cause the filtered liquid to move at a higher speed along capillary channel 25 than for the actuation that causes the filtered liquid to contact reagent portion 41 and/or for the actuation that causes the filtered liquid to contact detection zone 43.

The reader is actuated to determine the presence and/or amount of one or more targets. The reader may include a biosensor to determine the presence and/or amount of the one or more targets. The biosensor may be an electrochemical, optical, electro-optical, or acoustic mechanical detector. For example, the reader may include a light source and light detector to determine the presence and/or amount of detectable label bound in detection zone 43. The reader may be configured to disconnect gasket 105 of pump 101 prior to the step of detecting.

In use, the total volume of filtered liquid that is drawn into capillary channel 25 is less than a total volume of the capillary channel so that filtered liquid does not exit vent 29 of microfluidic device 20.

A distal portion of capillary channel 25 includes a distal stop 111 having a capillary break 113. Liquid reaching capillary break 113 experiences a reduced capillary force reducing a tendency of the liquid from advancing further along capillary channel 25. A depth of distal stop 111 is 300 microns. The depth of distal stop 111 is typically at least about 200 microns, at least about 250 microns, or at least about 275 microns. The depth of distal stop 111 may be about 1000 microns or less, about 750 microns or less, or about 500 microns or less. A width of channel 25 within distal stop 111 is about 1 mm. Typically, the width of channel 25 within distal stop 111 is at least about 500 microns, or at least about 750 microns. The width of channel 25 within distal stop 111 may be about 2500 microns or less, about 1500 microns or less or about 1250 microns or less.

Hydrophobic surfaces of microfluidic device 20, e.g., first, second, and third hydrophobic floor portions 71a, 71b, 71c, may be made hydrophobic using hydrophobic compounds, such as aliphatic and/or aromatic compounds and various inks and polymers and the like. The compounds are generally dissolved in organic solvents or mixtures of aqueous and organic solvents. U.S. Pat. No. 7,824,611 (incorporated by reference herein) discloses suitable techniques (such as ink jet printing, spraying, silk screening, drawing, embossing and the like) that permit the application of hydrophobic zones on or within surfaces.

For example, U.S. Pat. No. 7,824,611 discloses several techniques which may be utilized to make a surface hydrophobic. For surfaces made hydrophilic, hydrophobic zones can be created by application of organic solvents that destroy the plasma treatment or denature the proteins, to recreate a native hydrophobic plastic surface or to create a hydrophobic surface by the denatured proteins, or by local heating of the surface using focused laser beams to destroy the hydrophilic nature of the surface. Alternatively, one can mask hydrophobic areas before creating a hydrophilic area by any of the foregoing methods. The areas can be masked by objects such as a template or can be masked by materials that are applied to the surface and then are subsequently removed.

In one embodiment a hydrophobic surface may be created by beginning with a hydrophobic surface, such as are found on native plastics and elastomers (polyethylene, polypropylene, polystyrene, polyacrylates, silicon elastomers and the like). In an embodiment, hydrophobic particles, may be deposited upon a surface. Such particles include latex particles, for example polystyrene latexes with diameters of between about 0.01 µm and 10 µm or hydrophobic polymers, such as polypropylene, polyethylene, polyesters and the like. In another embodiment, a hydrophobic surface may be created by application of a hydrophobic chemical, such as an ink or a long chain fatty acid, or a hydrophobic decal to the desired zone. The hydrophobic chemical or decal is generally not soluble or is poorly soluble in the reaction mixture. In yet another preferred embodiment, the hydrophobic surface may be formed by changing a hydrophilic surface to a hydrophobic surface. For example, hydrophobic surfaces made hydrophilic by plasma treatment can be converted back to a hydrophobic surface by the application of solvents, ultraviolet light or heat and the like. These treatments can act to change the molecular structure of the hydrophilic, plasma modified surface back to a hydrophobic form.

As discussed above, hydrophobic compounds, such as aliphatic and/or aromatic compounds and various inks and polymers and the like can be used for the creation of hydrophobic zones in accordance with the invention. The compounds are generally dissolved in organic solvents or mixtures of aqueous and organic solvents. One skilled in the art will recognize that a variety of techniques known in the art (such as ink jet printing, spraying, silk screening, drawing, embossing and the like) are techniques that permit the application of hydrophobic zones on or within surfaces.

Components of microfluidic device 20 (e.g., lower and upper substrates 21,23) can be prepared from copolymers, blends, laminates, metallized foils, metallized films or metals. Alternatively, microfluidic device components can be prepared from copolymers, blends, laminates, metallized foils, metallized films or metals deposited one of the following materials: polyolefins, polyesters, styrene containing polymers, polycarbonate, acrylic polymers, chlorine containing polymers, acetal homopolymers and copolymers, cellulosics and their esters, cellulose nitrate, fluorine containing polymers, polyamides, polyimides, polymethylmethacrylates, sulfur containing polymers, polyurethanes, silicon containing polymers, glass, and ceramic materials. Lower and upper substrates 21,23 may be secured with respect to one another the various recesses and grooves sealed and the capillary cavities and channels formed by a number of techniques, including but not limited to, gluing, welding by ultrasound, riveting and the like.

What is claimed is:

1. An immunoassay method for determining the presence of a target in a liquid sample, the method comprising:
    (a) introducing the liquid sample to a proximal portion of a capillary flow channel;
    (b) advancing the liquid sample at a first flow rate toward a distal portion of the capillary flow channel until at least a distal gas-liquid interface of the liquid sample contacts a conjugate disposed in dry form within the capillary flow channel, the conjugate comprising a binding agent having an affinity for the target;
    (c) subsequently, by increasing a gas pressure differential between a proximal gas-liquid interface of the liquid sample and the distal gas-liquid interface of the liquid sample, advancing the liquid sample at a second flow rate toward the distal portion of the capillary flow channel until at least the distal gas-liquid interface contacts a detection zone within the capillary flow channel, the detection zone comprising a second binding agent having an affinity for a complex comprising the conjugate and the target, the second flow rate being slower than the first flow rate; and
    (d) subsequently, by increasing the gas pressure differential between the proximal
    and distal gas-liquid interfaces of the liquid sample, advancing the liquid sample a third flow rate toward the distal portion of the capillary flow channel until at least a conjugate is (a) bound to the second binding agent and/or been advanced beyond the detection zone toward the distal end of the capillary flow channel
    (e) wherein any of the steps of "increasing a gas pressure differential" is performed by increasing a volume of gas in communication with the distal gas-liquid interface of the liquid sample.

2. The immunoassay method of claim 1, wherein the capillary flow channel is disposed within a microfluidic device.

3. The immunoassay method of claim 1, further comprising, after the step of introducing the liquid sample, advancing the liquid sample by capillary flow along the capillary flow channel until the gas pressure acting upon the distal gas-liquid interface stops the liquid sample from advancing further along the capillary flow channel.

4. The immunoassay method of claim 3, wherein the liquid sample is stopped prior to contacting the conjugate.

5. The immunoassay method of claim 3, wherein the liquid sample is stopped after contacting the conjugate.

6. The immunoassay method of claim 1, further comprising providing a fluidic connection between a pump and a distal portion of the capillary flow channel.

7. The immunoassay method of claim 6, wherein the step of providing a fluidic connection is performed prior to the step of introducing the liquid sample.

8. The immunoassay method of claim 6, comprising terminating the fluidic connection between the pump and the distal portion of the capillary flow channel and then detecting conjugate present in the detection zone.

9. The immunoassay method of claim 8, wherein the method comprising placing the microfluidic device in operable association with an optical reader for the microfluidic device.

10. The immunoassay method of claim 9, wherein the step of providing the fluidic connection comprises automatically positioning a proximal opening of the pump with respect to a distal opening of the capillary flow channel.

11. The immunoassay method of claim 1, wherein any of the steps of "increasing a gas pressure differential" is performed by actuating the pump.

12. The immunoassay method of claim 11, wherein actuating the pump increases a volume of gas in communication with the distal gas-liquid interface of the liquid sample.

13. The immunoassay method of any of claim 12, wherein the pump is a syringe pump.

14. The immunoassay method of claim 1, wherein the liquid sample experiences a capillary force within the capillary flow channel and the magnitude of a force applied to the liquid sample by the "gas pressure differential" is less than about 15 times the magnitude of the capillary force, less than about 10 times the magnitude of the capillary force, or less than about 5 times the magnitude of the capillary force.

15. The immunoassay method of claim 1 further comprising the step of detecting conjugate bound to the detection zone.

16. The immunoassay method of claim 15, wherein the step of detecting is performed while a volume of the detection zone is filled with liquid sample.

17. The immunoassay method of claim 15, wherein the detection zone has a volume and the step of detecting is performed after removing a majority of the liquid sample from the detection zone.

18. The immunoassay method of claim 17, wherein the step of detecting is performed while a majority of the volume of the detection zone is occupied by a gas.

19. The immunoassay method of claim 16 wherein the step of detecting is performed without first introducing a liquid other than the liquid sample into the detection zone.

20. The immunoassay method of claim 1, wherein the liquid sample comprises a biological sample obtained from a mammal, blood, or urine.

21. The immunoassay method of claim 20 wherein the liquid sample comprises a reagent and the liquid sample is formed by combining the reagent and the biological sample.

22. The immunoassay method of claim 21 wherein the step of combining is performed prior to introducing the biological sample to the capillary flow channel.

23. The immunoassay method of claim 1 wherein the liquid sample is a filtered liquid sample formed by passing a liquid sample through a filter.

24. The immunoassay method of claim 23, wherein the filter comprises pores and a size of the pores decreases proceeding from a proximal face of the filter toward a distal face of the filter.

25. The immunoassay method of claim 23, wherein the filtered liquid sample comprises plasma and the step of passing the liquid sample through the filter comprises filtering red blood cells from the liquid sample.

26. The immunoassay method of claim 23, wherein a total volume of blood is about 75 microliters or less, 50 microliters or less, 30 microliters or less, 20 microliters or less, such as about 15 microliters or less.

27. The immunoassay method of claim 1 wherein a total volume of the liquid sample is about 75 microliters or less, 50 microliters or less, 30 microliters or less, or 20 microliters or less.

28. The immunoassay method of claim 1 wherein a total volume of the liquid sample is about 15 microliters or less.

29. The immunoassay method of claim 1 wherein a total volume of the liquid sample is about 10 microliters or less.

30. An immunoassay method for determining the presence of a target in a liquid sample, the method comprising:
   (a) introducing the liquid sample to a proximal portion of a capillary flow channel;
   (b) advancing the liquid sample via capillary action at a first flow rate toward a distal portion of the capillary flow channel until at least a distal gas-liquid interface of the liquid sample contacts a conjugate disposed in dry form within the capillary flow channel, the conjugate comprising a binding agent having an affinity for the target, wherein the distal gas-liquid interface of the liquid sample is formed between the liquid sample and a gas enclosed in the capillary flow channel distal to the distal gas-liquid interface;
   (c) subsequently, increasing the volume of the enclosed gas thereby decreasing a pressure of the enclosed gas acting on the distal gas-liquid interface and advancing the liquid sample via capillary action at a second flow rate toward the distal portion of the capillary flow channel until at least the distal gas-liquid interface contacts a detection zone within the capillary flow channel, the detection zone comprising a second binding agent having an affinity for a complex comprising the conjugate and the target, the second flow rate being slower than the first flow rate; and
   (d) subsequently, increasing the volume of the enclosed gas thereby decreasing a pressure of the enclosed gas acting on the distal gas-liquid interface and advancing the liquid sample via capillary action at a third flow rate toward the distal portion of the capillary flow channel until at least a conjugate is (a) bound to the second binding agent and/or advanced beyond the detection zone toward the distal end of the capillary flow channel.

* * * * *